(12) United States Patent
Latham

(10) Patent No.: US 6,183,501 B1
(45) Date of Patent: Feb. 6, 2001

(54) HEAD AND SPINE COOLING DEVICE

(75) Inventor: Jeffrey Wade Latham, San Marcos, TX (US)

(73) Assignee: Jeffrey W. Latham, San Marcos, TX (US)

( * ) Notice: Under 35 U.S.C. 154(b), the term of this patent shall be extended for 0 days.

(21) Appl. No.: 09/215,988

(22) Filed: Dec. 18, 1998

(51) Int. Cl.[7] ................................................ A61F 7/00
(52) U.S. Cl. ...................... 607/109; 607/108; 607/112; 607/110
(58) Field of Search ........................... 607/96, 108, 109, 607/110, 112

(56) References Cited

U.S. PATENT DOCUMENTS

| | | | | |
|---|---|---|---|---|
| 4,190,054 | * | 2/1980 | Brennan | 128/402 |
| 4,204,543 | | 5/1980 | Henderson | 128/402 |
| 4,356,709 | | 11/1982 | Alexander | 62/530 |
| 4,382,446 | | 5/1983 | Truelock et al. | 128/402 |
| 4,538,597 | | 9/1985 | Lerman | 128/75 |
| 4,552,149 | * | 11/1985 | Tatsuki | 128/402 |
| 4,576,169 | | 3/1986 | Williams | 128/402 |
| 4,732,144 | | 3/1988 | Cunanan | 128/878 |
| 4,750,493 | | 6/1988 | Brader | 128/380 |
| 4,805,619 | | 2/1989 | Swearingen | 128/380 |
| 4,815,144 | | 3/1989 | Martin | 2/7 |
| 5,054,475 | | 10/1991 | Calabrese et al. | 128/75 |
| 5,197,292 | | 3/1993 | McPherson | 62/56 |
| 5,211,623 | | 5/1993 | Sarkozi | 602/18 |
| 5,261,399 | * | 11/1993 | Klatz et al. | 607/104 |
| 5,327,585 | | 7/1994 | Karlan | 2/7 |
| 5,437,612 | | 8/1995 | Moore et al. | 602/171.2 |
| 5,551,807 | | 9/1996 | Hujar et al. | 2/171.2 |
| 5,913,885 | * | 6/1999 | Klatz et al. | 607/104 |
| 5,957,964 | * | 9/1999 | Ceravolo | 607/109 |
| 5,987,581 | * | 4/1999 | Fronda et al. | 607/109 |

OTHER PUBLICATIONS

Kobayashi Healthcare, Inc., add for "Mentholatum Migraine Ice Cooling Headache Pads for Migraine Sufferers," 2 pages.

Steele Incorporated, adds for "Hold and Cold Therapy, The Steelevest Body Cooling System," Mar. 1996, 8 pages.

Life Enhancement Technologies, Inc., "Let Personal Cooling System," 2 pages.

(List continued on next page.)

*Primary Examiner*—Linda C. M. Dvorak
*Assistant Examiner*—Jocelyn D Ram
(74) *Attorney, Agent, or Firm*—Sanford E. Warren, Jr.; Matthew E. Burr; Gardere & Wynne, L.L.P.

(57) ABSTRACT

A cooling system for the head, neck, and spine to reduce swelling caused by trauma to the brain is disclosed comprising a head device having a front panel and a back panel, a neck brace supporting the head device using a front rigid member and a back rigid member, and a cooling medium that cools the head device when activated.

14 Claims, 5 Drawing Sheets

OTHER PUBLICATIONS

Multiple Sclerosis Association of America, "MSAA Cooling and Multiple Sclerosis," 1997, 12 pages.

Jorgen Kinnman, M.D., Ph.D., Ulf Andersson, M.D., Ph.D., Ylva Kinnman, M.D. and Lill Wetterqvist, "Temporary Improvement of Motor Function in Patients with Multiple Sclerosis After Treatment with a Cooling Suit," J. Neuro Rehab. 1997, vol. 11, No. 2, pp. 109–114.

Charles Bechtel, Peter Damiri, Adam Roberts and Neal Zoren, "Keeping Cool," The Motivator, Jul./Aug. 1999, pp. 8–11.

Texan Corporation, "P.A.C. Tubing personal cooling system," Feb. 1999, 3 pages.

Microclimate Systems, Inc., "Advanced Technology, Personal Body Cooling System," 9 pages.

Yu–Tsuan E. Ku, Leslie D. Montgomery, MS, Ph.D., Karen C. Wenzel, MA CTRS/CLP, Bruce W. Webbon, MS, Ph.D. and Jack S. Burks, M.D., "Physiologic and Thermal Repsonses of Male and Female Patients with Multiple Sclerosis to Head and Neck Cooling," CME Article, 1999, pp. 447–451.

America Online: Sjkbits, "Bike Helmet a Must Even in Heat," Oct. 4, 1999, 2 pages.

* cited by examiner

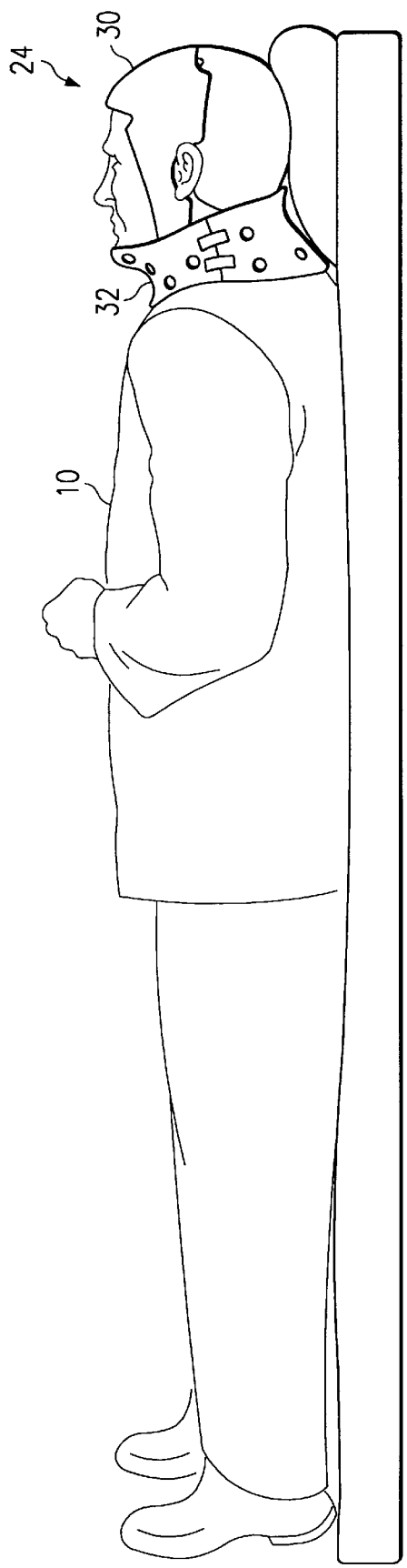
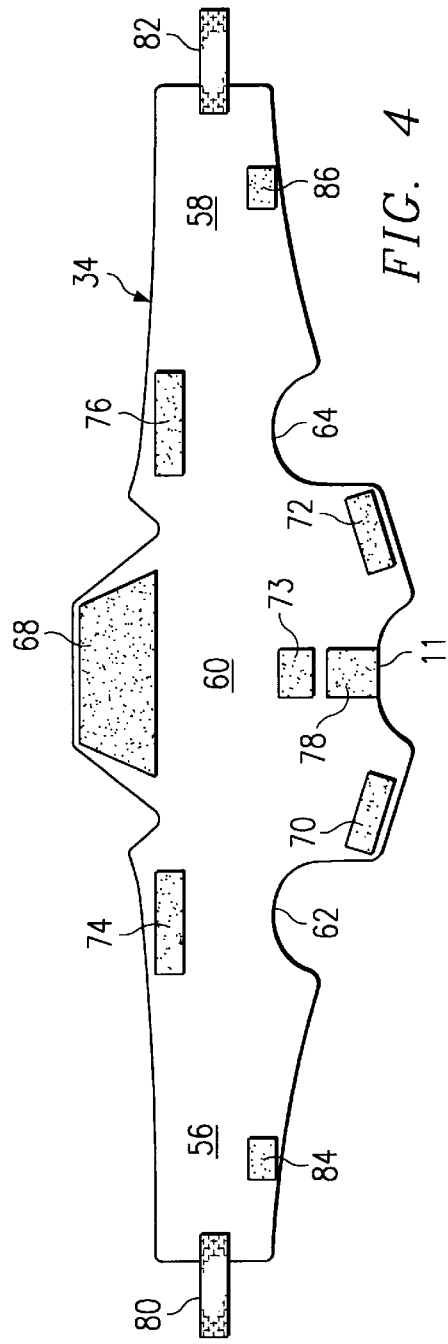
FIG. 2
FIG. 4

FIG. 5
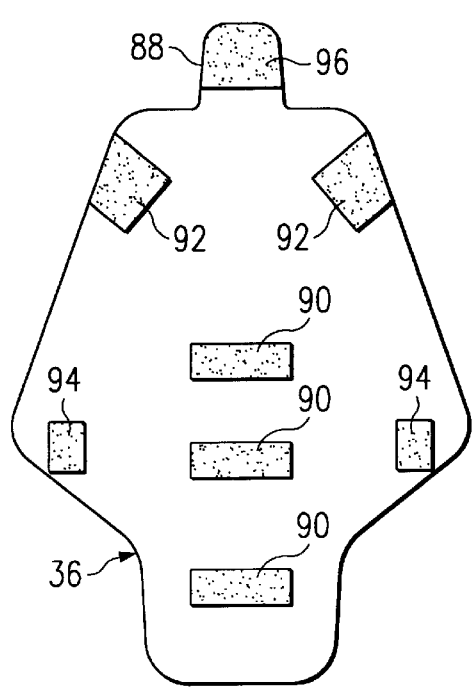
FIG. 5A
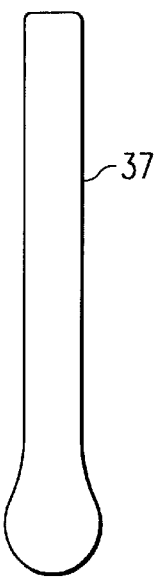
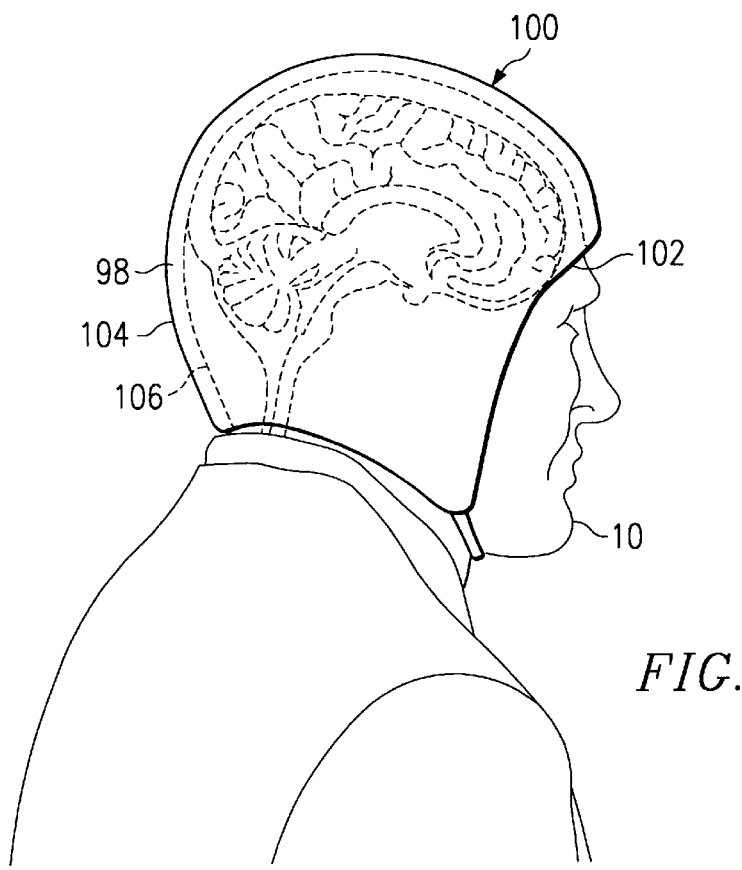
FIG. 6

HEAD AND SPINE COOLING DEVICE

TECHNICAL FIELD OF THE INVENTION

The present invention relates, in general, to the field of head, neck, and spine medical treatment, and more particularly, to a cooling device for the brain and spinal cord of an individual with a brain or spinal cord injury for reducing trauma to those areas.

BACKGROUND OF THE INVENTION

Without limiting the scope of the invention, its background is described in connection with brain and spinal cord treatment, as an example.

The brain and spinal cord form the central nervous system (CNS), the body's chief controlling and coordinating centers. The brain, which is housed in the skull, is the major organ of the body for control of all the body's voluntary and involuntary activities. The principal parts of the brain are the brain stem, the diencephalon, the cerebrum, and the cerebellum. Cranial bones and the cranial meninges protect the brain and cerebrospinal fluid serves as a shock absorber for the brain and circulates nutritive substances from the blood to the brain. A large round hole called the foramen magnum is located at the bottom of the skull. It is through the foramen magnum that the spinal cord passes down from the brain into the spine. The spine is a bony column which serves as a protective surrounding for the spinal cord.

When an area of the body collides with an external source in its surroundings, severe trauma and swelling of the tissue may occur in the injured area. To reduce swelling, treatment often consists of lowering the temperature of the injured area.

Lowering temperature is often achieved by applying a cold element or substance to the injured area. In some instances, the treatment has been as simple as applying ice to the location of the injury. More sophisticated methods have included applying cold packs to the injury. Heretofore, in this field, cold therapy has generally been limited to the limbs of the body including the leg (particularly the knee), the arm, and the shoulder. Treatment of this type has generally been applied most consistently in situations involving athletic injuries. Cold therapy has also been used for aesthetic purposes such as applying cold packs to the face to reduce bags under the eyes and for purposes of reducing the pain of headaches. Therapy has generally required refrigeration of the packs.

When the brain or spinal cord is traumatized due to injury, the extent of the trauma to the brain or spinal cord is not always readily apparent. The collision of an individual's head with external surroundings causes the brain to collide with the individual's skull, which may produce welling of the brain. Swelling can restrict the flow of fluids that normally circulate around the brain and, potentially, cause the fluids to accumulate and therefore compress the brain down into the floor of the skull and cervical bone of the spine. The collision of the individual's head or body with external surroundings may cause injury to the spinal cord and result in swelling. To reduce the effects of this secondary trauma, the present invention can be placed over the head, neck, and spinal regions to lower the temperature in those areas and help reduce swelling. The reduced swelling of the brain reduces the potential for more serious injury to the individual.

Therefore, there is a need for a device that may be easily transported and applied in emergency situations but may also be used in rehabilitative environments. Also, there is a need for a device that requires no special storage conditions such that implementation of such a device requires extensive redesign of, or requires, additional space for storage facilities. Furthermore, there is a need for a device that may be flexibly and easily adapted to a individual at the scene of an accident while not adding additional stress or pressure on the individual.

SUMMARY OF THE INVENTION

The present invention disclosed herein is a cooling system that includes a head and neck device which can be cooled to reduce trauma to the brain. The cooling device facilitates cooling of the head and neck which reduces swelling of the brain. Reduction of swelling of the brain helps to decrease both short and long term damage to the brain of a patient.

In one embodiment, the cooling system includes a head device and a neck brace. The head device has a front panel and a back panel; each panel capable of housing a cold element to facilitate cooling. The front panel may include a plurality of fastening devices to secure the head device to the head of the individual. The front panel may also include a plurality of orifices to facilitate access to the ears of the individual. The back panel of the head piece may include a plurality of fastening devices and a bottom appendage; the fastening device being positioned to come into contact with the plurality of fastening devices located on the front panel for complete coverage of the head and over the carotid arteries. The back panel may be elongated by attaching a back panel strip that covers the back along the spinal cord for cooling.

The cooling system may also include a neck brace having front and back brace members and a chin support. The neck brace may further include a plurality of orifices that allow air to circulate to reduce heat buildup which may cause sweating and discomfort of the individual. The neck brace may also have a hole for, e.g., facilitating a tracheotomy to assist the individual in breathing, if necessary. The neck brace may also include a fastening device to secure the neck brace to the individual and to support the head device.

In another embodiment, the cooling system of the present invention may be a one-piece head device. The head device includes an opening for facial exposure and is capable of housing a cooling element. The head device further includes a flexible material.

In yet another embodiment, the cooling system of the present invention comprises a cooling device and a cooling element system. The cooling element system includes a connecting mechanism whereby the cooling element may enter the cooling device, a storage device for housing said cooling element, and a release system.

The present invention allows Emergency Medical Services (EMS) personnel to monitor bleeding of the individual, if any. The present invention also facilitates management of the airway by allowing for tracheotomy treatment. Because of the facial opening of the present invention, the eyes, nose and mouth of the individual may be monitored.

BRIEF DESCRIPTION OF THE DRAWINGS

For a more complete understanding of the features and advantages of the present invention, reference is now made to the detailed description of the invention along with the accompanying figures in which corresponding numerals in the different figures refer to corresponding parts and in which:

FIG. 2 is a schematic illustration of one embodiment of the present invention as placed on an accident individual portraying the left side view;

FIG. 4 is a schematic illustration of the top view of the top panel of the head device of one embodiment of the present invention;

FIG. 5 is a schematic illustration of the top view of the back panel of the head device of one embodiment of the present invention;

FIG. 6 is a schematic illustration of another embodiment of the present invention as placed on a medical patient portraying the t side view.

DETAILED DESCRIPTION OF THE INVENTION

The present invention disclosed herein includes a head device and a cooling medium for cooling the head and spine. Cooling of the head and spine facilitates a reduction in swelling of the brain and surrounding tissue after injury, which helps to minimize long term damage to the brain. The present invention also encompasses a method for using the head device and for activating the cooling material to facilitate cooling of the brain after an injury.

It has been reported that approximately 20 percent of all head injuries are classified as severe and hence may be potentially life threatening. The overall effects of traumatic brain injuries are permanent and complex, thus, management of traumatic brain injury is of critical importance. Management of the effects of the injuries during the critical time period following severe brain injury or during what professionals in emergency medicine have termed the golden hour affects the survival and recovery of those individuals. This golden hour includes the time the patient is at the scene of the accident and the essential field stabilization and transport of the individual to a medical facility. The golden hour also includes a window of opportunity to determine how extensive the damage is to the brain. Neurologists may need to perform a CT scan to evaluate the extent of damage to the brain and to determine if there are bleeds, lesions contusions to the brain, and/or fractures to the skull. On-scene intervention also includes procedures that are as unobtrusive as possible and limit damage to the brain. Current emergency protocols require checking airway, breathing, and circulation (ABC's)followed by neck and spinal stabilization when neck and back injury appears to be evident before transport.

Figure 1:
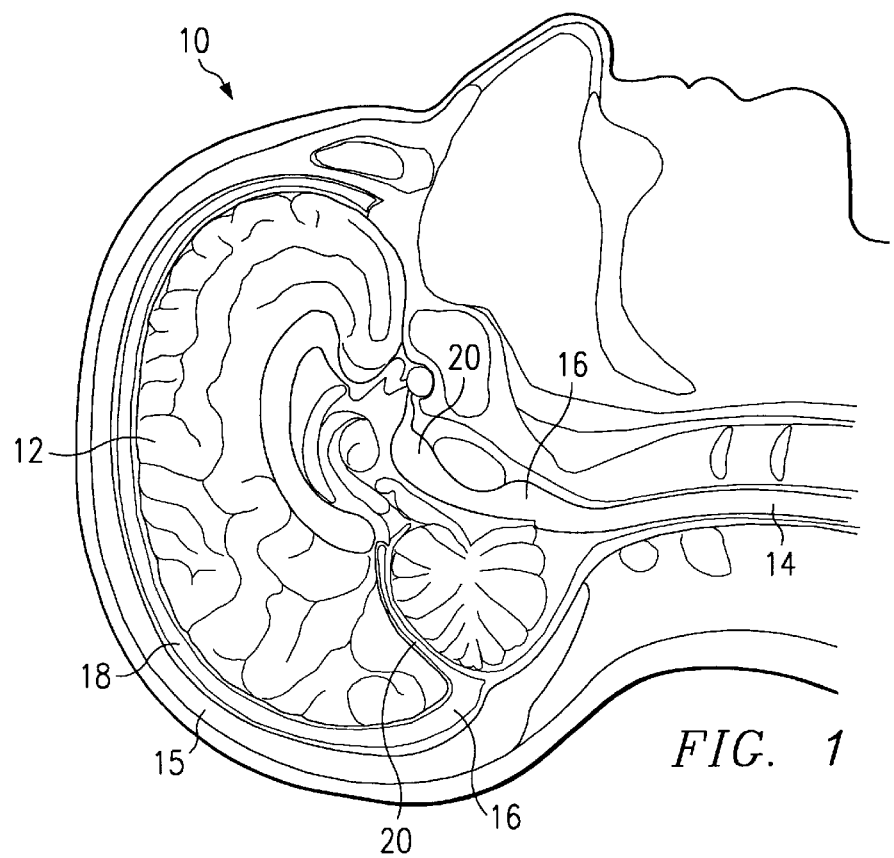
FIG. 1 is a cross sectional view of the brain with cerebrospinal fluid.

FIG. 1 is a cross sectional view of the brain with cerebrospinal fluid. The brain 12, as well as the spinal cord 14, is generally protected against injury by cerebrospinal fluid 16. The cerebrospinal fluid 16 circulates through the subarachnoid space 18 that is around the brain 12 and spinal cord 14. The cerebrospinal fluid 16 also circulates through the brain 12 via ventricles 20. Normally, cerebrospinal fluid 16 is absorbed as rapidly as it is formed. Cerebrospinal fluid generally leaves the body at the same rate it is produced, about 0.47 milliliters per hour, through the arachnoid space 18 at the top of the skull 15. The cerebrospinal fluid 16 is a clear, colorless, fluid having a watery consistency and contains vital nutrients including proteins, glucose, salts, and white blood cells. The cerebrospinal fluid 16 also circulates nutrients delivered via the blood.

Figure 1A:
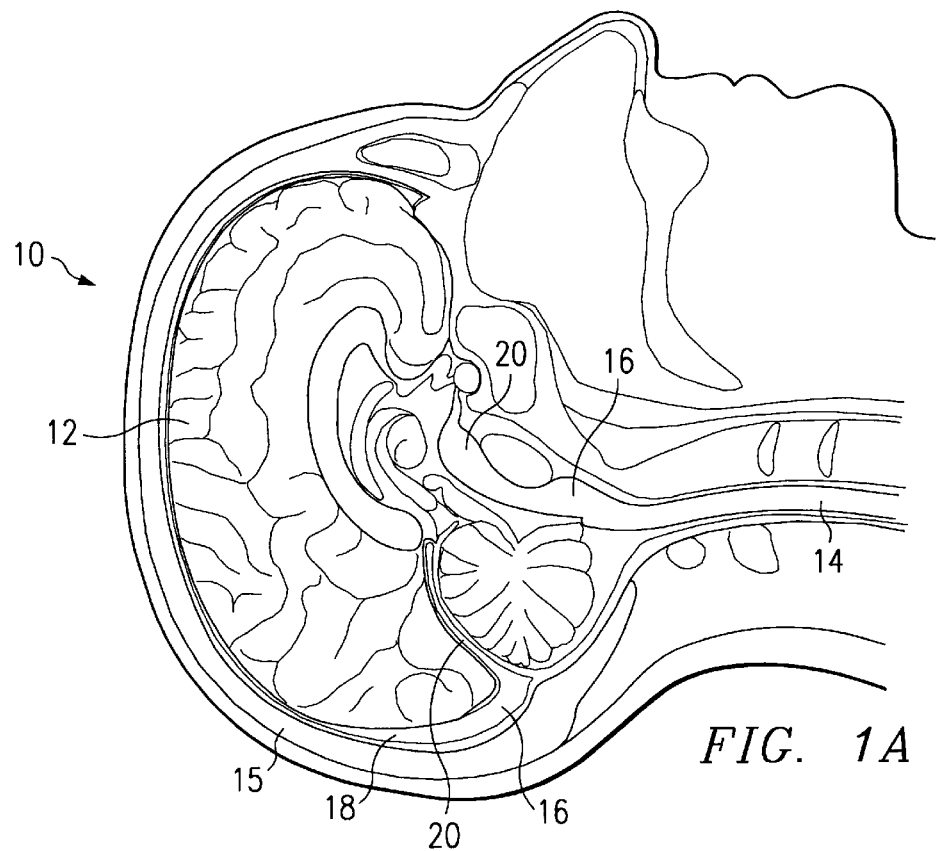
FIG. 1a is a cross sectional view of the brain with cerebrospinal fluid after a traumatic injury.

FIG. 1a is a cross sectional view of a brain having swelled against the skull 15 designated as 22. When a brain injury occurs there is primary physical damage that can kill or disable. But there are also secondary insults to the brain 12, which result from the swelling of the brain 12. When swelling occurs, the brain 12 will swell against the skull 15, thus blocking the flow of the cerebrospinal fluid 16 around the brain 12 and blocking the flow of nutrients through the ventricles 20. The internal pressure builds and squeezes blood vessels blocking the flow of blood which carries oxygen and nutrients to the brain. A reduction in the flow of nutrients to the brain 12 also causes secondary damage to the brain 12. The build up of fluids 16 causes inter-cranial pressure (ICP) to build and the brain swells against the skull and blocks the exit point of cerebrospinal fluid 16. The brain also becomes damaged by pressing against the wall of the skull. All of the above cause additional or secondary injury to the brain. The elevation of the heart rate increases more blood to the injured area of the brain, thereby causing more damage due to swelling and the presence of blood destroying brain cells.

The present inventor has recognized that application of a cold element to the head, neck, and/or spine reduces the swelling of the brain and spinal cord after an injury and reduces the increased flow of blood by means of cooling the carotid artery. Reducing swelling is particularly important in emergency situations such as vehicle accidents which involve head and/or spinal cord injuries as there is eminent potential for build up of blood and cerebrospinal fluid in the cranial cavity. Damage is further intensified because the heart rate is increased as a natural response to trauma, thereby increasing profusion pressure (more blood to the injured site). In the case of penetrating or open head injuries, the problem of increased pressure due to blockage or exit capabilities is naturally reduced as the skull has been penetrated, but reducing the flow of blood to the area may help to reduce the amount of hemorrhaging.

FIG. 2 is a schematic illustration of one embodiment of the present invention as placed on an accident individual. The accident individual 10 is found immobile at the scene of the accident. Emergency Medical Services (EMS) has standard guidelines by which treatment is administered to brain and spinal cord injury individuals. EMS will perform the ABC's and make an assessment using the Glascow Coma Scale (GCS) which assesses the person's level of consciousness by eye opening, visual tracking, response to pain, and environmental stimulation to determine if a brain injury is suspected. If the person is unconscious, the stabilization of the head, neck, and back is completed. EMS personnel will be able to place the cooling system 24 on the head of the individual 10 in order to reduce intercranial pressure consequently reducing trauma to the brain and in turn, reducing or minimizing brain damage. The cooling system 24 is mounted on the head and neck of individual 10 through the use of head device 30 and neck brace 32. The cooling system 24 stabilizes and cools the head and neck of individual 10. The use of the cooling system 24 can be used in addition to current neurological protocols as an effort to reduce the need for a shunt, thereby reducing the need for invasive procedures to an already injured site.

Figure 3:
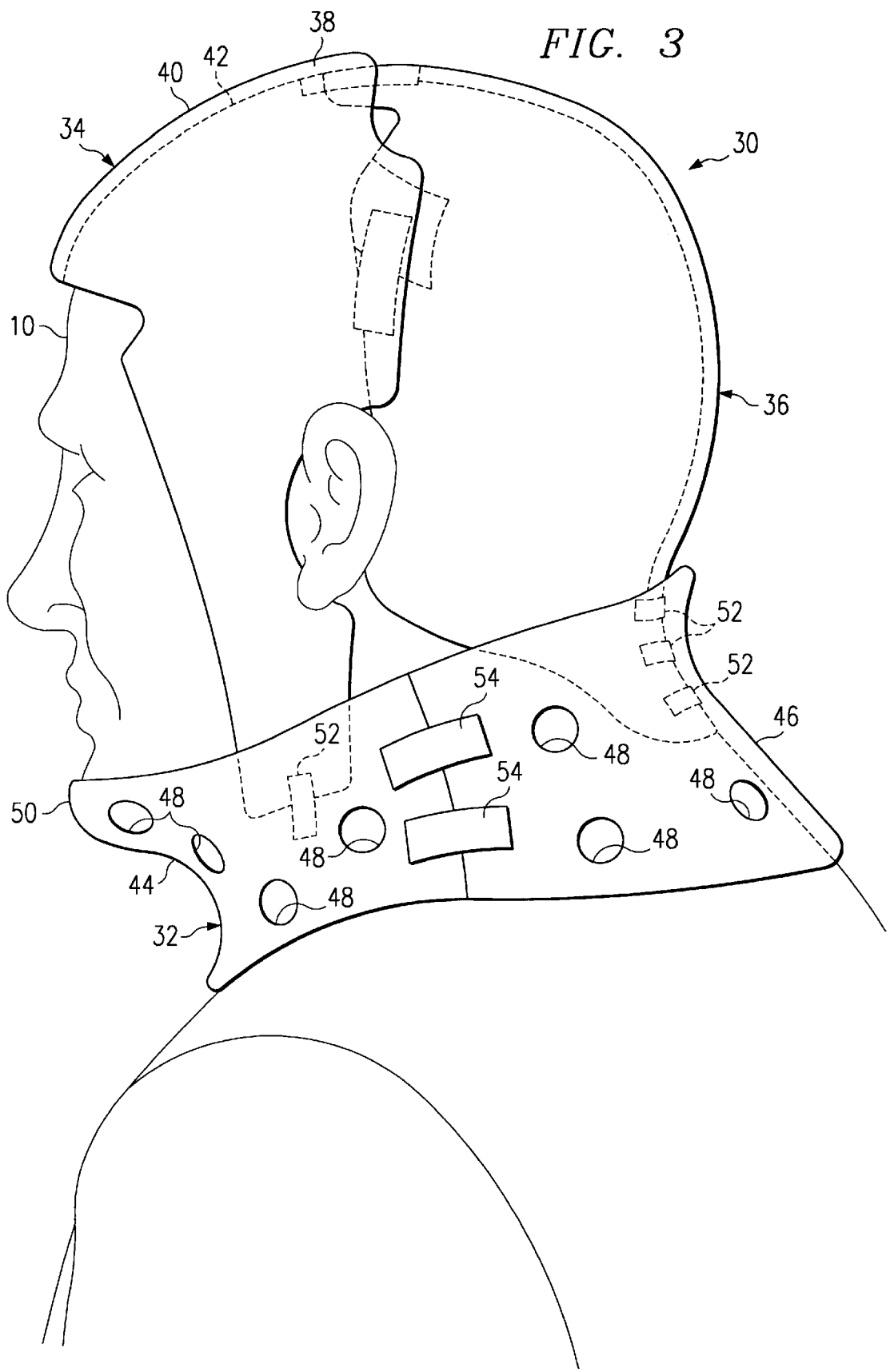
FIG. 3 is a schematic illustration of the left side view of one embodiment of the present invention in application.

Referring to FIG. 3, the head device 30 includes a top panel 34, a back panel 36, and a back panel strip 37 all of which are made of flexible material 38. Flexible material 38 may be, e.g., plastic, flexible foam, cloth, paper, or rubber. The flexible material 38 may have non-metallic properties that allow the head device 30 to be worn into a magnetic resonance imaging ("MRI")machine after individual 10 is brought to a medical facility. Head device 30 also includes a top layer 40 and bottom layer 42 that allow the cooling properties of cooling system 24 to be activated.

The neck brace 32 may include a front brace member 44, a back brace member 46, and a plurality of orifices 48 for air circulation. Neck brace 32 may also include a chin support 50 that permits the neck brace 32 to be more comfortably fitted to individual 10. The brace members 44 and 46 may include a plurality of inside fastening devices 52 and a plurality of outside fastening devices 54, that permit the brace members 44 and 46 to be fastened and permit the head device 30 to be interfaced to the neck brace 32 and provide a rigid support for the head of individual 10.

Referring to FIG. 4, the top panel 34 having a substantially rectangular shape has a first elongated member 56, a second elongated member 58, and a central portion 60. The elongated members 56 and 58 extend from the central portion 60 of the top panel 34, which permit the central portion 60 to be positioned on top of the head of individual 10. The elongated members 56 and 58 are generally flush with the sides of the face of individual 10. Elongated member 56 and 58 extend down to facilitate cooling of the carotid arteries. The first and second elongated members 56 and 58 include a first recess 62 and a second recess 64, respectively, to provide openings for the ears of individual 10. Accessibility to the ears of individual 10 allows EMS to provide medical treatment, if necessary, as bleeding from the ears can result from traumatic brain injuries. Accessibility to the ears of individual 10 also allows the patient to hear EMS personnel. The central portion 60 may include a third recess 71 for the hair of individual 10. The top panel 34 may further include a fastening device 68 (located on central portion 60), a left panel fastening device 70 and right panel fastening device 72 (also located on central portion 60). Left panel fastening device 70 is generally located below and adjacent fastening device 68 and is generally parallel to right panel fastening device 72, which is located below and to the right of the fastening device 68. The fastening devices 68, 70, and 72 are positioned to moveably connect to a fastening strap 73 that secures the head device 30 to individual 10.

The top panel 34 may also include a first and second reflective member 74 and 76, respectively, whereby the head of individual 10 is readily visible in dark and low visibility conditions. The top panel 34 may also include a bottom fastening device 78 located on central portion 60 that permits the back panel 36 to be connected and provides full coverage of the head of individual 10. The top panel 34 may also include left and right end tabs 80 and 82, located at the ends of elongated members 56 and 58 ,respectively. Located adjacent of end tabs 80 and 82 are end fastening devices 84 and 86.

Now referring to FIG. 5, the back panel 36 is depicted having an appendage 88, a first plurality of fastening devices 90, a second plurality of fastening devices 92, and a third plurality of fastening devices 94. The plurality of first fastening devices 90 are generally positioned in parallel on back panel 36 and used to connect the back panel 36 to the neck brace 32. The second plurality of fastening devices 92 are fixedly attached to the back panel 36 and connect the sides of back panel 36 to the elongated members 54 and 56 of the front panel 34. The appendage 88 has an appendage fastening device 96 fixedly attached to the appendage 88.

The appendage fastening device 96 of appendage 88 and the third plurality of fastening devices 94 attach to the cooling strap 73 to secure the head device 30 to the head of individual 10. A back panel strip 37 (FIG. 5a) may be attached to the back panel 36 to facilitate cooling of the spinal cord area.

The cooling medium 98 may be any substance that provides cooling properties to the head device. The cooling medium may include chemical packets that are activated by application of pressure to the packet resulting in an endothermic reaction. The cooling medium may also include ice or generic ice packs that are refrigerated. The cooling medium generally will lower the temperature of the head approximately one to approximately two degrees and may include a large number of packets or changing of packets at predetermined intervals such that the head is cooled.

FIG. 6, depicts another embodiment of the present invention. The cooling system has a head piece 100 having an opening 102 and a cooling medium 98 which allows the face to be exposed for sight and breathing by the individual 10. The head piece 100 has a top layer 104 and bottom layer 106 and the cooling medium 98. The head piece 100 is suitable for non-emergency situations athletic events, such as boxing, where repeated blows to the head occur. The head piece 100 may also be worn when needed by traumatic brain injury patients that are in rehabilitation therapy when needed. Trauma to the brain requires extensive rehabilitation, which may lead to swelling from time to time and which causes setbacks in recovery. Patients in rehabilitation will generally feel a heating sensation. Such swelling and sensation may be reduced by application of the head piece 100.

Figure 7:
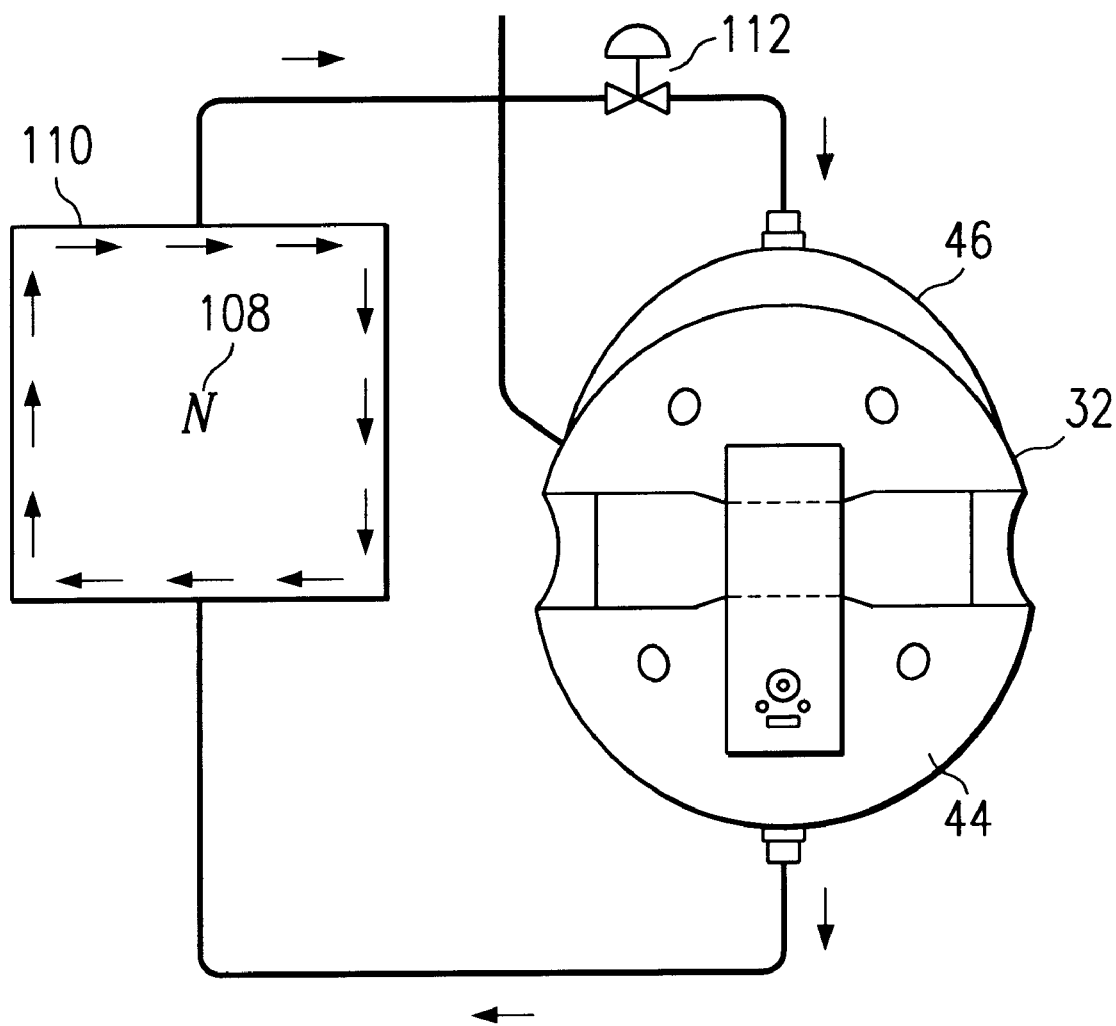
FIG. 7 is a frontal view of yet another embodiment of the present invention having a cooling element system fluidly connected to the head device.

FIG. 7 is cross-sectional view of yet another embodiment of the present invention. The neck brace 32 and cooling medium system 108 function as integral parts of the neck brace 32. Circulated through the front brace member 44 and the back brace member 46 are a chemical or chemical mixtures that act as coolants. The chemical or chemical mixtures are contained in a tank 110, and their circulation is regulated by valves 112 that are interconnected to the front brace member 44 and the back brace member 46. The flow of chemicals allows for immediate reduction of swelling of the brain and may be, e.g. constant, intermittent or under the control of a temperature gauge or feed back system.

OPERATION

In operation, if cooling medium 98 is resident in head device 30, such as a single-use or replaceable package, then cooling medium 98 is simply activated and the device 30 is placed on the patient. If the cooling medium 98 is stored outside the head device 30, the cooling medium 98 is activated and then placed within the head device 30. The cooling system 24 is then mounted on the head of individual 10.

The cooling system 24 is mounted by first placing the back panel 36 flat into the inside of back brace member 46 followed by aligning the first plurality of fastening devices 90 of back panel 36 with the inside fastening devices 52 of back brace member 46. Fastening devices 90 and 52 are then connected. The top layer 40 of back panel 36 should face the inside of back brace member 46 such that the third plurality of fastening devices 94 of back panel 36 are unencumbered by the back brace member 46. The combined back panel 36 and back brace member 46 are then carefully and strategically positioned to the back of the head of individual 10.

Next, the top panel 34 of head device 30 is placed on the top portion of the head of individual 10 with the top fastening device 68 of front panel 34 facing the face of individual 10. Once front panel 34 has been positioned so as to cover the top of individual's 10 head, elongated members 56 and 58 are brought down and around the individual's 10 face to the right and left respectively. As the two elongated members 56 and 58 are lowered, a first recess 62 and a second recess 64 are comfortably positioned around the ears of individual 10 within the recesses 62 and 64. The fastening device 68 of front panel 34 sits in close proximity to the eyes but generally do not cover them. The fastening device 78 of top panel 34 is attached to the fastening device 96 of back panel 36, providing full coverage of the head. The reflective members 74 and 76 should generally be readily visible at each side of the elongated members 56 and 58. The two elongated members 56 and 58 will generally meet at the bottom of individual's 10 chin. The left-end fastening device 80 and the right- end fastening device 82 allow, e.g., EMS, to pull gently to snugly fit to head of individual 10.

The front brace member 44 is placed around the front of individual's 10 neck and the elongated members 56 and 58 such that the chin of individual 10 sits comfortably in the chin support 50 of front brace member 44. The front and back brace members 44 and 46 will generally meet such that the plurality of fastening devices are connected to secure the entire cooling system. The cooling strap 73 is then applied centeredly to the front fastening device 96 of top panel 34. Finally, the cooling strap is brought around to attach to the second plurality of fastening devices 92 of top panel 34.

The foregoing description has been directed to particular embodiments of the invention in accordance with the Patent Statutes for the purposes of illustration and explanation. It will be apparent that many alternatives, modifications, and variations will be apparent to those skilled in the art in light of the foregoing disclosure. In particular changes may be made to the shape and size of the head piece and neck brace to accomodate all patients, including humans and animals.

What is claimed is:

1. A cooling system for cooling the head and neck of an individual wearing the system, the system comprising:
    a top panel having a plurality of cooperating fasteners and having a right side and a left side corresponding to the right side and the left side, respectively, of said individual and further having a first elongate neck member at said right side and a second elongate neck member at said left side whereby said neck members are disposed substantially over the carotid arteries of the neck when worn by said individual;
    a back panel having a plurality of cooperating fasteners. whereby said top panel is adjustable fastenable to said back panel; and
    activatable cooling medium housed in said top panel and said back panel wherein said cooling medium cools the head and cools blood flowing to the head from the carotid arteries of the neck upon activation of said cooling medium.

2. The cooling system as recited in claim 1 wherein said top and back panels comprise a flexible material that conforms to the head and neck of an individual.

3. The cooling system as recited in claim 1 wherein said elongate neck members each further comprise a perimeter contour shaped to provide access to the ears of said individual.

4. The cooling system as recited in claim 1, further comprising a neck. brace, wherein said top panel having a plurality of fasteners is moveably fastenable to said neck brace.

5. The cooling system as recited in claim 4 wherein said back panel further comprises a fastener whereby said back panel is moveably fastenable to said neck brace.

6. The cooling system as recited in claim 4 wherein said neck brace further comprises a flexibly rigid material for support of the neck.

7. The cooling system as recited in claim 4 wherein said neck brace further comprises a plurality of openings for air ventilation and breathing assistance.

8. The cooling system as recited in claim 4 wherein said neck brace further comprises a front brace member and a back brace member.

9. The cooling system as recited in claim 8 wherein said neck brace further comprises a plurality of connecting members and said front brace member is secured to said back brace member.

10. The cooling system as recited in claim 8 wherein said front brace member further comprises a chin support. activation of said cooling medium.

11. The cooling system as recited in claim 4 wherein said neck brace is further defined as comprising at least one orifice allowing access to the neck of said individual.

12. The cooling system as recited in claim 1 wherein said system comprises a third member housing activable cooling medium whereby said third member is moveably attached to said back panel to provide cooling of the spine upon activation of said cooling medium.

13. The cooling system as recited in claim 1 further comprising a cooling medium reservoir housing said activatable cooling medium and a connecting means whereby said cooling medium in said cooling medium reservoir is in fluid communication with said cooling system, wherein said cooling medium is circulated for cooling of said head and neck of said individual.

14. A method for mounting a cooling system to the head and neck of an individual having a brain or spine injury comprising the steps of:
    providing a device having top and back panels and a neck brace having front and back members;
    providing cooling medium in the device;
    activating the cooling medium;
    interfacing the back panel to the back member to form an integrated unit;
    placing the integrated unit on the back of the head of the individual;
    placing the top panel on the top of the individual's head;
    placing the front member on the front of the individual's neck;
    interfacing the top panel to the front member; and
    interfacing the front member to the back member.

* * * * *